United States Patent [19]
Cerbelaud et al.

[11] Patent Number: 5,089,405
[45] Date of Patent: * Feb. 18, 1992

[54] PROCESS FOR THE PREPARATION OF OPTICALLY ACTIVE 2-ARYLPROPIONIC ACIDS AND PHARMACEUTICAL COMPOSITIONS CONTAINING THE SAME

[75] Inventors: Edith Cerbelaud; Dominique Petre, both of Lyons, France

[73] Assignee: Rhone-Poulenc Sante, Antony Cedex, France

[*] Notice: The portion of the term of this patent subsequent to Jul. 23, 2008 has been disclaimed.

[21] Appl. No.: 385,084

[22] Filed: Jul. 26, 1989

Related U.S. Application Data

[63] Continuation-in-part of Ser. No. 302,192, Jan. 27, 1989, abandoned.

[30] Foreign Application Priority Data

Jan. 27, 1988 [FR] France ................... 88 00923

[51] Int. Cl.$^5$ ............................. C12P 7/40
[52] U.S. Cl. ........................ 435/136; 435/141; 435/280; 514/568
[58] Field of Search ............ 435/280, 136, 141

[56] References Cited

U.S. PATENT DOCUMENTS 3,940,316  2/1976  Commeyras et al. .
4,366,250  12/1982  Jallageas et al. .
4,812,403  3/1989  Boesten et al. ............... 435/115

FOREIGN PATENT DOCUMENTS 187680   7/1986  European Pat. Off. .
227078   7/1987  European Pat. Off. .
1342844  10/1963  France .
2447359  8/1980  France .
949669   2/1964  United Kingdom .
8607386  12/1986  World Int. Prop. O. .

OTHER PUBLICATIONS

Zbl. Bakt. Hyg., I. Abt. Orig. A220, 452–456 (a1972) Frommer et al.,
Chemical Abstracts, vol. 91, 1979, p. 610.
25 Noncondensed Aromatics, vol. 83, 1975, pp. 471–472 (27810).
Chemical Abstracts, vol. 81, 1974, p. 376.
Thiery et al, Chem. Abst., vol. 105 (1986), p. 167, 595W.
Dotani et al, Chem. Abst., vol. 104 (1986), p. 166,912Q.

*Primary Examiner*—Sam Rosen
*Attorney, Agent, or Firm*—Morgan & Finnegan

[57] ABSTRACT

S Enantiomers of 2-arylpropionic acids are made by enantioselective hydrolysis of the corresponding racemic 2-arylpropionamides in the presence of a microorganism, or of an enzyme derived therefrom, able selectively to hydrolyze racemic α-phenylpropionamide to S α-phenylpropionic acid. The S Enantiomers obtained may be incorporated into antiinflammatory, analgesic and antipyretic compositions.

9 Claims, No Drawings

PROCESS FOR THE PREPARATION OF OPTICALLY ACTIVE 2-ARYLPROPIONIC ACIDS AND PHARMACEUTICAL COMPOSITIONS CONTAINING THE SAME

This application is a continuation-in-part of application Ser. No. 302,192 filed Jan. 27, 1989, now abandoned.

The present invention relates to the preparation of optically active 2-arylpropionic acids of general formula:

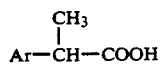

in which Ar denotes an unsubstituted or substituted monocyclic or polycyclic aromatic radical or an unsubstituted or substituted aromatic heterocyclic radical, by enantioselective hydrolysis of the corresponding racemic amides.

More particularly, the present invention relates to the preparation of the S enantiomers of 2-arylpropionic acids which have antiinflammatory properties. Among therapeutically active 2-arylpropionic acids there may be mentioned, for example, ketoprofen, naproxen, ibuprofen, suprofen, fenoprofen, benoxaprofen, carprofen, cicloprofen, pirprofen, flurbiprofen and fluprofen. Still more particularly, the present invention relates to the preparation of the S (+) enantiomer of 2-(3-benzoylphenyl)propionic acid [S (+) ketoprofen].

It is known to prepare the S enantiomers of 2-arylpropionic acids by stereoselective oxidation of 2-arylpropanes by means of fungi and yeasts (EP-A-205,215) or by stereospecific hydrolysis of the racemic esters by a lipase of extracellular or microbial origin (EP-A-227,078).

It is also known (FR 79/01,803/2,447,359) to prepare optically active α-amino acids by biological hydrolysis of α-amino nitriles using an agent containing a general nitrilase and a stereospecific L amidase or of α-amino amides by using an agent containing a stereospecific L amidase. The agents employed are bacteria or acellular preparations of bacterial origin containing a stereospecific L amidase, which originate from the mutation of strains containing a general amidase. The hydrolysis of the α-amino nitriles or of the α-aminoamides produces a mixture of L α-aminoacid and of D α-aminoamide; it being possible for the D α-aminoamide to be hydrolyzed to a D α-aminoacid using an agent containing a general amidase and containing no racemase.

It has now been found, and this forms the subject matter of the present invention, that racemic 2-arylpropionamides can be hydrolyzed enantioselectively to 2-aryl-propionic acids of general formula (I) in S form using a microorganism, or an enzyme derived therefrom, chosen for its ability selectively to hydrolyze racemic α-phenyl-propionamide to S α-phenylpropionic acid.

The selection of the agent (microorganism or enzyme) which promotes the enantioselective hydrolysis of the racemic 2-arylpropionamide is made by bringing the agent into contact with racemic α-phenylpropionamide in a suitable medium until 20% of the amide is converted, and then measuring the enantiomeric excess. An agent which, under these conditions, hydrolyzes racemic α-phenylpropionamide to S α-phenyl-propionic acid with an enantiomeric excess greater than 65% is suitable for use in the present invention.

Particularly suitable microorganisms belong to the genera Brevibacterium and Corynebacterium and, more particularly, to the species Brevibacterium R 312 (CBS 717.73), Corynebacterium N 771 (FERM P 4445), and Corynebacterium N 774 (FERM P 4446), which make it possible to obtain S 2-arylpropionic acids with an enantiomeric excess of S isomer greater than 90%.

It is surprizing to find that, among these microorganisms, Brevibacterium R 312, which is described in FR 79/01,803/2,447,359, published Aug. 22, 1980, in which it is stated that that microorganism has been deposited with the Centraal Bureau voor Schimmelcultures, Oosterstraat 1, PO Box 273, 3740, AG Baarn, Netherland, as CBS 717 73, and in Advances in Biochemical Engineering, vol. 14, p. 1-32 (1980) as containing a non-stereospecific general amidase, hydrolyzes racemic 2-arylpropionamides stereospecifically, while its $A_4$ mutant which contains a stereospecific L amidase does not hydrolyze racemic 2-arylpropionamides stereoselectively.

It should also be noted that Corynebacterium N 771 and Corynebacterium N 774, which are described in EP 0,187,680, in which it is stated that these microorganisms were deposited with the Fermentation Research Institute, Agency of Science and Technology, 1,3-Higashi 1-Chome, Yatabe-machi, Tsukuba-gun, Ibaraki-ken, Japan, on May 30 1978 as FERM P-4445 and FERM P-4446 respectively, hydrolyze, for example, lactonitrile to D,L lactic acid and α-amino-phenylpropionitrile to D,L-phenylalanine, with no stereoselectivity.

The process of the present invention is generally operated in a homogeneous or heterogeneous, aqueous or aqueous organic medium, under temperature and pH conditions which are determined by the nature of the microorganism and of the enzyme, by agitating a suspension of cells, or of a cell extract of the microorganism, and the racemic 2-arylpropionamide.

The process produces a mixture of S 2-arylpropionic acid and of R 2-arylpropionamide. The R 2-arylpropionamide may then be racemized by known methods to racemic 2-arylpropionamide, which can be again hydrolyzed to S 2-arylpropionic acid under the conditions described above. For example, the racemization of R 2-arylpropionamide may be carried out by heating in aqueous ammonia at a temperature of between 80° and 160° C.

When the microorganism employed has the property of hydrolyzing nitriles, combined with the property of enantioselectively hydrolyzing α-phenylpropionamide, an S 2-arylpropionic acid can be obtained either from the racemic 2-arylpropionitrile (which is hydrolyzed in situ to racemic 2-arylpropionamide) or from the racemic 2-arylpropionamide.

The process of the present invention is particularly suitable for preparing S (+) ketoprofen from racemic 2-(3-benzoylphenyl)propionamide or racemic 2-(3-benzoylphenyl)propionitrile.

EXAMPLES

The following Examples illustrate the invention.

EXAMPLE 1 a) The strain Brevibacterium R 312 (CBS 717.73) is cultured in an agitated flask at 28° C. for 14 hours in a medium having the composition.

| | |
|---|---|
| Glucose | 10 g |
| (NH₄)₂SO₄ | 5 g |
| KH₂PO₄ | 1.01 g |
| Na₂HPO₄.12H₂O | 1.64 g |
| K₂HPO₄ | 0.82 g |
| CaCl₂.2H₂O | 0.012 g |
| ZnCl₂ | 0.0012 g |
| FeSO₄.7H₂O | 0.0012 g |
| MnSO₄.H₂O | 0.0012 g |
| MgSO₄.7H₂O | 0.5 g |
| Thiamine hydrochloride | 0.002 g |
| Water q.s. | 1000 cc |

This preculture is employed for inoculating a culture medium having the same composition but additionally containing N-methylacetamide at the concentration of 20 mM. The culture is produced in an agitated flask kept for 24 hours at 28° C. The biomass obtained is separated by centrifuging and is then washed twice with a solution of sodium chloride at a concentration of 9 g/liter.

b) A centrifugation pellet containing Brevibacterium R 312 cells (13 mg, expressed as solids content) is suspended in phosphate buffer (50 mM; 2 cc) at pH=7. Racemic 2-phenylpropionitrile (25 mg, 190 μmol) is added. After 24 hours' agitation at 25° C., the reaction mixture is diluted by adding a mixture of acetonitrile and N hydrochloric acid (90/10 by volume, 23 cc). The bacteria are removed by centrifuging. The composition of the supernatant is determined by high performance liquid chromatography (HPLC).

The supernatant contains:
2-phenylpropionamide (119 μmol)
2-phenylpropionic acid (62 μmol.

Sodium chloride is added to promote the separation of the aqueous or organic phases. After evaporating the organic phase to dryness, the residue is taken up with a mixture of chloroform and 0.1N sodium hydroxide (1/1 by volume; 20 cc). The basic phase is acidified and is then extracted with chloroform. Measurement of rotatory power of the extracted 2-phenylpropionic acid shows that the enantiomeric excess of S (+) isomer is 100%.

After forming a derivative of 2-phenylpropionic acid with R (+) α-methylbenzylamine, analysis by HPLC shows that the enantiomeric excess is 96.4%.

EXAMPLE 2 a) The strain Corynebacterium N 771 (FERM P 4445) is cultured in an agitated flask at 28° C. for 14 hours, in a medium having the following composition:
Yeast extract—3 g
Malt extract—3 g
Bactopeptone—5 g
Glucose—10 g
FeSO₄.7H₂O—0.1 g
Water q.s.—1 liter
and whose pH is adjusted to 7.5 by adding sodium hydroxide before sterilization.

This preculture is employed for inoculating in a ratio of 1/40 a medium of the same composition, to which a solution of ketoprofen nitrile in acetonitrile (0.2 g/cc) is added in a proportion of 5 cc per liter.

After incubation for 24 hours at 28° C. in an agitated flask, the biomass is separated by centrifuging and is then washed twice with an aqueous solution of sodium chloride (9 g/liter).

b) A centrifugation pellet containing Corynebacterium N 771 cells (72 mg, expressed as solids content) is suspended in phosphate buffer (50 mM; 2 cc) at pH=7. Racemic 2-phenylpropionamide (25 mg, 167 μmol) is added, followed by agitating for 24 hours at 25° C. The reaction mixture is treated under the conditions of Example 1.

The supernatant contains:
2-phenylpropionamide (110 μmol)
2-phenylpropionic acid (34 μmol).

The enantiomeric excesses of 2-phenylpropionic acid, measured using the rotatory power and after forming a derivative with R (+) α-methylbenzylamine, are 100 and 95% as S (+) isomer, respectively.

EXAMPLE 3

A centrifugation pellet obtained under the conditions of Example 1 a), containing Brevibacterium R 312 cells (13 mg, expressed as solids content) is suspended in phosphate buffer (50 mM; 2 cc) at pH=7. Racemic 2-phenylpropionamide (25 mg, 167 μmol) is added. The mixture is agitated for 24 hours at 25° C. The reaction mixture is treated under the conditions of Example 1.

The supernatant contains:
2-phenylpropionamide (95.2 μmol)
2-phenylpropionic acid (56.1 μmol).

The enantiomeric excesses of 2-phenylpropionic acid, measured by the rotatory power and after forming a derivative with R (+) α-methylbenzylamine, are 99 and 95% as S (+) isomer, respectively.

EXAMPLE 4

A centrifugation pellet obtained under the conditions of Example 1 a), containing Brevibacterium R 312 cells (66 mg, expressed as solids content) is suspended in potassium phosphate buffer (50 mM; 2 cc) at pH=7. Racemic 2-(3-benzoylphenyl)propionamide (25.9 mg, 102 μmol) is added. The mixture is agitated for 72 hours at 25° C. The reaction mixture is diluted by adding a mixture of acetonitrile and N hydrochloric acid (90/10 by volume; 23 cc). The bacteria are removed by centrifuging. The supernatant, analyzed by high performance liquid chromatography, contains:
Ketoprofen (46 μmol)
Ketoprofen amide (59 μmol).

Sodium chloride is added to promote the separation of the aqueous and organic phases. After evaporating the organic phase to dryness, the residue is taken up with a mixture of chloroform and 0.1N sodium hydroxide (1/1 by volume; 20 cc).

The basic phase is acidified and is then extracted with chloroform. After forming the R (+) α-methylbenzylamine derivative of ketoprofen, analysis of the mixture of the two diastereoisomers by high performance liquid chromatography shows that the enantiomeric excess of S (+) ketoprofen is 93%.

EXAMPLE 5

A pellet containing Corynebacterium N 771 cells (180 mg, expressed as solids content), obtained under the conditions of Example 2 a), is suspended in potassium phosphate buffer (50 mM; 2 cc) at pH=7. Racemic ketoprofen amide (25.3 mg, 100 μmol) is added. After agitating for 48 hours at 25° C., a mixture of acetonitrile and N hydrochloric acid (90/10 by volume; 23 cc) is added. The bacteria are removed by centrifuging. The supernatant, analyzed by high performance liquid chromatography, contains:
Ketoprofen amide (76.03 μmol)
Ketoprofen (24.7 μmol).

A few mg of sodium chloride are added. The aqueous and organic phases separate. After evaporating the organic phase to dryness, the residue is taken up with a mixture of chloroform and 0.1N sodium hydroxide (1/1 by volume; 20 cc). The aqueous phase is acidified and is then extracted with chloroform. After forming the R (+) α-methylbenzylamine derivative of ketoprofen, analysis of the mixture of the two diastereoisomers by high performance liquid chromatography shows that the enantiomeric excess of S (+) ketoprofen is 94%.

EXAMPLE 6

A centrifugation pellet, obtained under the conditions of Example 1 a), containing Brevibacterium R 312 cells (24 mg, expressed as solids content), is suspended in potassium phosphate buffer (50 mM; 2 cc) at pH=7. Racemic 2-(3-benzoylphenyl)propionitrile (ketoprofen nitrile) (23.5 mg, 100 μmol) is added. After agitating for 65 hours at 25° C., a mixture of acetonitrile and N hydrochloric acid (90/10 by volume; 23 cc) is added. The bacteria are removed by centrifuging. The supernatant, analyzed by high performance liquid chromatography, contains:

Ketoprofen nitrile (2.2 μmol)
Ketoprofen amide (53 μmol)
Ketoprofen (44.7 μmol).

A few mg of sodium chloride are added. The aqueous and organic phases separate. After evaporation of the organic phase to dryness, the residue is taken up with a mixture of chloroform and 0.1N sodium hydroxide (1/1 by volume; 20 cc). After separation, the organic phase is evaporated to dryness. The residue (13.5 mg) containing ketoprofen amide is diluted with chloroform (2 cc). Measurement of the rotatory power of this solution shows that the enantiomeric excess of R (−) ketoprofen amide is 84%.

The aqueous phase, which is basic, is acidified and is then extracted with chloroform. After formation of the R (+) α-methylbenzylamine derivative of ketoprofen, analysis of the two diastereoisomers by high performance liquid chromatography shows that the enantiomeric excess of S (+) ketoprofen is 96%.

EXAMPLE 7

A Corynebacterium N 774 (FERM P 4446) cell pellet is prepared under the conditions described in Example 2 a) for the preparation of a Corynebacterium N 771 pellet.

A cell pellet containing 176 mg of cells, expressed as dry solids, is suspended in potassium phosphate buffer (50 mM; 2 cc) at pH=7. Racemic ketoprofen amide (25.3 mg, 100 μmol) is added. After agitating for 48 hours at 25° C., the reaction mixture is treated under the conditions of Example 1.

Analysis of the reaction mixture shows that it contains:

Ketoprofen amide (78.6 μmol)
Ketoprofen (22.4 μmol).

The enantiomeric excess of ketoprofen as S (+) isomer, determined after derivative formation, is 95%.

EXAMPLE 8

Active, optically pure ketoprofen amide (20 mg, 79 μmol) is introduced into a 5-cc autoclave containing aqueous ammonia (28% w/v; 1 cc). After being closed, the autoclave is placed for 2 hours in an oven at 150° C. After cooling, the contents of the autoclave are poured into water (5 cc). The pH is adjusted to 1 by adding 1N hydrochloric acid. The aqueous phase is extracted with chloroform. The chloroform phase is dried over sodium sulphate. After filtration, the volume is adjusted to 2 cc by concentration.

The rotatory power of this chloroform solution is zero.

Analysis by HPLC shows that this solution contains ketoprofen amide (72.2 μmol) and ketoprofen (4.1 μmol).

The present invention includes within its scope antiinflammatory, analgesic and antipyretic compositions containing, as active ingredient, an S-2-aryl-propionic acid prepared by the new process, and especially S (+) 2-(3-benzoylphenyl) propionic acid, or pharmaceutically-acceptable salt thereof, in association with a pharmaceutical carrier or coating. The invention includes especially such preparations made up for oral, parenteral or rectal administration, or topical application, e.g. as ointments or creams.

Solid compositions for oral administration include tablets, pills, powders, and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting, emulsifying and suspending agents, and sweetening, flavoring and aromatizing agents. The compositions according to the invention, for oral administration, also include capsules of absorbable material such as gelatin containing the active substance with or without the addition of diluents or excipients.

Preparations according to the invention for parenteral administration include sterile aqueous or non-aqueous solutions, suspensions, or emulsions. For such preparations suitable solvents or vehicles are propylene glycol, a polyethylene glycol, vegetable oils such as olive oil, and injectable organic esters such as ethyl oleate. The compositions may also contain adjuvants such as wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as onono butter or a suppository wax.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. In human therapy the compositions should be administered so as to give between 10 and 500 mg. of active substance per day, usually by the oral route.

The following Examples illustrate pharmaceutical compositions according to the invention.

EXAMPLE A

Tablets weighing 175 mg. and having the following composition are prepared:

| | |
|---|---|
| S (+) 2-(3-benzoylphenyl)propionic acid | 25 mg. |
| Starch | 120 mg. |
| Colloidal silica | 27 mg. |
| Magnesium stearate | 3 mg. |

EXAMPLE B

Tablets weighing 500 mg. and having the following composition are prepared:

| | |
|---|---|
| S (+) 2-(3-benzoylphenyl)propionic acid | 250 mg. |
| Starch | 190 mg. |
| Colloidal silica | 50 mg. |
| Magnesium stearate | 10 mg. |

EXAMPLE C

Injectable compositions having the following composition are prepared:

| | |
|---|---|
| S (+) 2-(3-benzoylphenyl)propionic acid | 25 mg. |
| Arginine | 18.3 mg. |
| Citric acid sufficient quantity for pH = | 6.5 |
| Injectable medium | 2 cm$^3$ |

EXAMPLE D

Gel composition having the following composition are prepared:

| | |
|---|---|
| S (+) 2-(3-benzoylphenyl)propionic acid | 0.75 g |
| Gel agent | 0.9 g |
| Neutralizing agent | 1.8 g |
| Ethyl alcohol | 8.1 g |
| Distilled water sufficient quantity for | 30 g |

We claim:

1. A process for the preparation of an S enantiomer of 2-arylpropionic acid of formula:

$$Ar-\overset{\overset{\displaystyle CH_3}{|}}{CH}-COOH$$

in which Ar represents a phenyl radical substituted by 3-benzoyl, which comprises hydrolyzing enantioselectively a corresponding racemic 2-arylpropionamide, which may be prepared in situ, in the presence of a microorganism, or an enzyme derived therefrom, able selectively to hydrolyze racemic α-phenylpropionamide to S α-phenylpropionic acid with an enantiomeric excess greater than 65%, and then separating S 2-arylpropionic acid obtained from R 2-arylpropionamide.

2. Process according to claim 1, wherein the microorganism has nitrilase activity as well as the ability enantioselectively to hydrolyze racemic α-phenylpropionamide to S α-phenylpropionic acid.

3. Process according to claim 2, wherein the racemic 2-arylpropionamide is produced in situ by the enzymatic hydrolysis of racemic 2-arylpropionitrile.

4. Process according to claim 1, wherein the microorganism is a Brevibacterium or Corynebacterium.

5. Process according to claim 1, wherein the microorganism is Brevibacterium R 312 (CBS 717-73), Corynebacterium N 771 (FERM P 4445) or Corynebacterium N 774 (FERM P 4446).

6. Process according to claim 3, wherein the microorganism is a Brevibacterium or Corynebacterium.

7. Process according to claim 6, wherein the microorganism is Brevibacterium R 312 (CBS 717.73), Corynebacterium N 771 (FERM P 4445) and Corynebacterium N 774 (FERM P 4446).

8. Process according to claim 1, wherein S (+) 2-(3-benzoylphenyl)propionic acid is formed from racemic 2-(3-benzoylphenyl)propionamide or from racemic 2-(3-benzoylphenyl)propionitrile.

9. Process according to claim 1, wherein the S-2-arylpropionic acid obtained is incorporated into an antiinflammatory analgesic or antipyretic composition containing also a pharmaceutical carrier or coating.

* * * * *